United States Patent
Annis

(10) Patent No.: US 7,705,160 B2
(45) Date of Patent: Apr. 27, 2010

(54) METHOD FOR PREPARING 3-HALO-4,5-DIHYDRO-1H-PYRAZOLES

(75) Inventor: Gary David Annis, Landenberg, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 42 days.

(21) Appl. No.: 12/004,902

(22) Filed: Dec. 21, 2007

(65) Prior Publication Data

US 2008/0108821 A1    May 8, 2008

Related U.S. Application Data

(63) Continuation of application No. 10/518,325, filed as application No. PCT/US03/23820 on Jul. 29, 2003, now Pat. No. 7,335,780.

(60) Provisional application No. 60/446,451, filed on Feb. 11, 2003, provisional application No. 60/400,356, filed on Jul. 31, 2002.

(51) Int. Cl.
*C07D 231/08* (2006.01)
(52) U.S. Cl. .............................. 548/379.1; 548/374.1
(58) Field of Classification Search .............. 548/379.1, 548/374.1
See application file for complete search history.

(56) References Cited

U.S. PATENT DOCUMENTS

| 3,577,471 A | 5/1971 | McNulty et al. |
|---|---|---|
| 2004/0198984 A1 | 10/2004 | Lahm et al. |
| 2004/0198987 A1 | 10/2004 | Freudenberger et al. |
| 2004/0209923 A1 | 10/2004 | Berger et al. |
| 2005/0075372 A1 | 4/2005 | Lahm et al. |
| 2005/0215785 A1 | 9/2005 | Taylor |

FOREIGN PATENT DOCUMENTS

| GB | 1 410 191 A | 10/1975 |
|---|---|---|
| WO | WO 01/70671 | 9/2001 |
| WO | WO 03/016263 A1 | 2/2003 |
| WO | WO 2004/011447 A3 | 2/2004 |

OTHER PUBLICATIONS

J.P. Chupp, New Regional Isomers of 1-Methyl-6-(Trifluoromethyl) Pyrazoles, J. Heterocyclic Chem., vol. 31, 1377-1380, 1994.
M.V. Gorelik et. al., Structure and Properties of Pyrazolinediazonium Salts, Zhurnal Organicheskio Khimii, vol. 21 (4), 851-859, 1985.
K.K. Bach et. al., 1,3-Dipolar Cycloadditions of Ethoxycarbonyl-Nitrile, -Tetrahedron, vol. 50 (25), 7543-7556, 1994.
Jose Elguero et. al., Recherches Dans La Serie Des Azoles, Bulletin De La Societe Chimique De France, vol. 5, 1663-1686, 1969.
Abstract Re. Wendler; Tishler; JACSAT; Journal of the American Chemical Society; 71; 1949; 374; DOI: 10.1021.
Abstract Re; Chang et al.; JACSAT; Journal of American Chemical Society; 79; 1957; 2164, 2167; DOI 10.1021.

*Primary Examiner*—Elvis O Price

(57) ABSTRACT

This invention relates to a method for preparing a 3-halo-4,5-dihydro-1H-pyrazole compound of Formula I

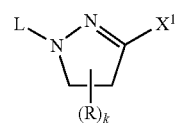

comprising contacting with $HX^1$ a different 4,5-dihydro-1H-pyrazole compound of Formula II

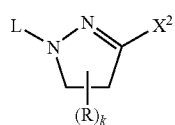

wherein $X^1$ is halogen and L, R, k and $X^2$ are as defined in the disclosure. This invention also discloses preparation of compounds of Formula III

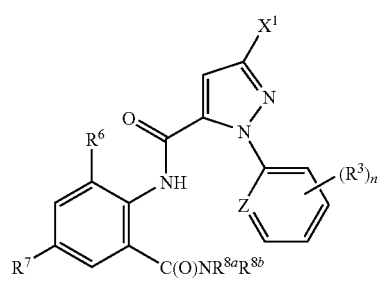

wherein $X^1$, $R^3$, $R^6$, $R^7$, $R^{8a}$, $R^{8b}$ and n are as defined in the disclosure.

10 Claims, No Drawings

METHOD FOR PREPARING 3-HALO-4,5-DIHYDRO-1H-PYRAZOLES

This application is a continuation of U.S. patent application Ser. No. 10/518,325 filed Feb. 15, 2004 (issued as U.S. Pat. No. 7,335,780 on Feb. 26, 2008) which represents a national filing under 35 U.S.C. 371 of International Application No. PCT/US2003/023820 filed Jul. 29, 2003, and claims priority of U.S. Provisional Application No. 60/446,451 filed Feb. 11, 2003 and U.S. Provisional Application No. 60/400,356 filed Jul. 31, 2002.

BACKGROUND OF THE INVENTION

A need exists for additional methods to prepare 3-halo-4,5-dihydro-1H-pyrazoles. Such compounds include useful intermediates for the preparation of crop protection agents, pharmaceuticals and other fine chemicals.

Several methods have been reported for the preparation of 3-halo-4,5-dihydro-1H-pyrazoles. For example, J. P. Chupp, *J. Heterocyclic Chem.* 1994, 31, 1377-1380 reports the preparation of a 3-chloro-4,5-dihydro-1H-pyrazole by contacting the corresponding oxo-pyrazolidine with phosphorus oxychloride. M. V. Gorelik et al., *Journal of Organic Chemistry U.S.S.R.* 1985, 21, 773-781 (English language translation of *Zhurnal Organicheskoi Khimii* 1985, 21(4), 851-859) discloses the preparation of 3-chloro-4,5-dihydro-1H-pyrazoles by way of diazonium salt intermediates prepared from the corresponding 3-amino-4,5-dihydro-1H-pyrazoles. K. K. Bach et al., *Tetrahedron* 1994, 50(25), 7543-7556 discloses the preparation of a 3-chloro-4,5-dihydro-1H-pyrazole by dipolar cycloaddition of an acrylate ester with a hydrazidoyl chloride intermediate formed by decarboxylative chlorination of a hydrazone of glyoxylic acid using N-chlorosuccinimide. The need remains for alternative methods, particularly those of broad chemical structure generality and which use relatively low cost reagents commercially available in industrial quantities.

SUMMARY OF THE INVENTION

This invention relates to a method for preparing a 3-halo-4,5-dihydro-1H-pyrazole compound of Formula I

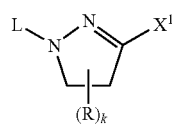

wherein L is an optionally substituted carbon moiety;
each R is independently selected from optionally substituted carbon moieties;
k is an integer from 0 to 4;
and $X^1$ is halogen.

The method comprises contacting a 4,5-dihydro-1H-pyrazole compound of Formula II

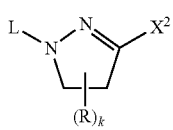

wherein $X^2$ is $OS(O)_m R^1$, $OP(O)_p(OR^2)_2$ or a halogen other than $X^1$;
m is 1 or 2;
p is 0 or 1;
$R^1$ is selected from alkyl and haloalkyl; and phenyl optionally substituted with from 1 to 3 substituents selected from alkyl and halogen; and
each $R^2$ is independently selected from alkyl and haloalkyl; and phenyl optionally substituted with from 1 to 3 substituents selected from alkyl and halogen;

with a compound of the formula $HX^1$ in the presence of a suitable solvent.

This invention also relates to a method of preparing a compound of Formula III,

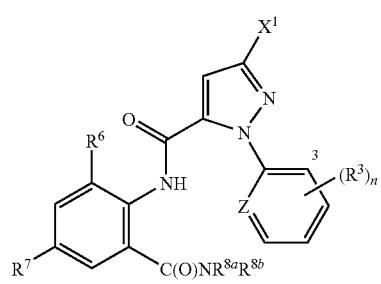

wherein
$X^1$ is halogen;
each $R^3$ is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, ($C_1$-$C_4$ alkyl)($C_3$-$C_6$ cycloalkyl)amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;
Z is N or $CR^5$;
$R^5$ is H or $R^3$;
$R^6$ is $CH_3$, F, Cl or Br;
$R^7$ is F, Cl, Br, I or $CF_3$;
$R^{8a}$ is $C_{1-4}$ alkyl;
$R^{8b}$ is H or $CH_3$; and
n is an integer from 0 to 3 using a compound of Formula Ia

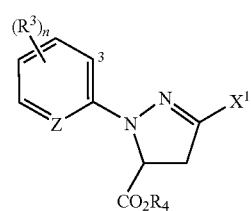

wherein $R^4$ is H or an optionally substituted carbon moiety.

This method is characterized by preparing the compound of Formula Ia (i.e. a subgenus of Formula I) by the method as indicated above.

DETAILED DESCRIPTION OF THE INVENTION

In the recitations herein, the term "carbon moiety" refers to a radical in which a carbon atom is connected to the backbone of the 4,5-dihydro-1H-pyrazole ring. As the carbon moieties L and R (including $R^4$) are substituents separated from the reaction center, they can encompass a great variety of carbon-based groups preparable by modern methods of synthetic organic chemistry. The method of this invention is generally applicable to a wide range of starting compounds of Formula I and product compounds of Formula II. One skilled in the art will recognize that certain groups are sensitive to hydrogen halides and may be transformed under the reaction conditions. One skilled in the art will also recognize that certain groups are basic and can form salts with hydrogen halides, and thus the method of this invention can require additional hydrogen halide.

"Carbon moiety" thus includes alkyl, alkenyl and alkynyl, which can be straight-chain or branched. "Carbon moiety" also includes carbocyclic and heterocyclic rings, which can be saturated, partially saturated, or completely unsaturated. Furthermore, unsaturated rings can be aromatic if Hückel's rule is satisfied. The carbocyclic and heterocyclic rings of a carbon moiety can form polycyclic ring systems comprising multiple rings connected together. The term "carbocyclic ring" denotes a ring wherein the atoms forming the ring backbone are selected only from carbon. The term "heterocyclic ring" denotes a ring wherein at least one of the ring backbone atoms is other than carbon. "Saturated carbocyclic" refers to a ring having a backbone consisting of carbon atoms linked to one another by single bonds; unless otherwise specified, the remaining carbon valences are occupied by hydrogen atoms. The term "aromatic ring system" denotes fully unsaturated carbocycles and heterocycles in which at least one ring in a polycyclic ring system is aromatic. Aromatic indicates that each of ring atoms is essentially in the same plane and has a p-orbital perpendicular to the ring plane, and in which (4n+2) π electrons, when n is 0 or a positive integer, are associated with the ring to comply with Hückel's rule. The term "aromatic carbocyclic ring system" includes fully aromatic carbocycles and carbocycles in which at least one ring of a polycyclic ring system is aromatic. The term "nonaromatic carbocyclic ring system" denotes fully saturated carbocycles as well as partially or fully unsaturated carbocycles wherein none of the rings in the ring system are aromatic. The terms "aromatic heterocyclic ring system" and "heteroaromatic ring" include fully aromatic heterocycles and heterocycles in which at least one ring of a polycyclic ring system is aromatic. The term "nonaromatic heterocyclic ring system" denotes fully saturated heterocycles as well as partially or fully unsaturated heterocycles wherein none of the rings in the ring system are aromatic. The term "aryl" denotes a carbocyclic or heterocyclic ring or ring system in which at least one ring is aromatic, and the aromatic ring provides the connection to the remainder of the molecule.

The carbon moieties specified for L, R and $R^4$ are optionally substituted. The term "optionally substituted" in connection with these carbon moieties refers to carbon moieties that are unsubstituted or have at least one non-hydrogen substituent. Illustrative optional substituents include alkyl, alkenyl, cycloalkyl, cycloalkenyl, aryl, hydroxycarbonyl, formyl, alkylcarbonyl, alkenylcarbonyl, alkynylcarbonyl, alkoxycarbonyl, hydroxy, alkoxy, alkenyloxy, alkynyloxy, cycloalkoxy, aryloxy, alkylthio, alkenylthio, alkynylthio, cycloalkylthio, arylthio, alkylsulfinyl, alkenylsulfinyl, alkynylsulfinyl, cycloalkylsulfinyl, arylsulfinyl, alkylsulfonyl, alkenylsulfonyl, alkynylsulfonyl, cycloalkylsulfonyl, arylsulfonyl, amino, alkylamino, alkenylamino, alkynylamino, arylamino, aminocarbonyl, alkylaminocarbonyl, alkenylaminocarbonyl, alkynylaminocarbonyl, arylaminocarbonyl, alkylaminocarbonyl, alkenylaminocarbonyl, alkynylaminocarbonyl, arylaminocarbonyloxy, alkoxycarbonylamino, alkenyloxycarbonylamino, alkynyloxycarbonylamino and aryloxycarbonylamino, each further optionally substituted; and halogen, cyano and nitro. The optional further substituents are independently selected from groups like those illustrated above for the substituents themselves to give additional substituent groups for L, R and $R^4$ such as haloalkyl, haloalkenyl and haloalkoxy. As a further example, alkylamino can be further substituted with alkyl, giving dialkylamino. The substituents can also be tied together by figuratively removing one or two hydrogen atoms from each of two substituents or a substituent and the supporting molecular structure and joining the radicals to produce cyclic and polycyclic structures fused or appended to the molecular structure supporting the substituents. For example, tying together adjacent hydroxy and methoxy groups attached to, for example, a phenyl ring gives a fused dioxolane structure containing the linking group —O—$CH_2$—O—. Tying together a hydroxy group and the molecular structure to which it is attached can give cyclic ethers, including epoxides. Illustrative substituents also include oxygen, which when attached to carbon forms a carbonyl function. Similarly, sulfur when attached to carbon forms a thiocarbonyl function. Within a carbon moiety L or R, tying together substituents can form cyclic and polycyclic structures. Also illustrative of carbon moieties L and R are embodiments wherein at least two R moieties, or the L moiety and at least one R moiety, are contained in the same radical (i.e., a ring system is formed). As the 4,5-dihydropyrazole moiety constitutes one ring, two vicinally positioned R moieties, or L and R moieties, contained in the same radical would result in a fused bicyclic or polycyclic ring system. Two geminally positioned R moieties contained in the same radical would result in a spiro ring system.

As referred to herein, "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1-2 alkyl" indicates that one or two of the available positions for that substituent may be alkyl which are independently selected. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkenyloxy" includes straight-chain or branched alkenyloxy moieties. Examples of "alkenyloxy" include $H_2C$=$CHCH_2O$, $(CH_3)_2C$=$CHCH_2O$, $(CH_3)CH$=$CHCH_2O$, $(CH_3)CH$=$C(CH_3)CH_2O$ and $CH_2$=$CHCH_2CH_2O$. "Alkynyloxy" includes straight-chain or branched alkynyloxy moieties. Examples of "alkynyloxy" include HC≡$CCH_2O$, $CH_3C$≡$CCH_2O$ and $CH_3C$≡$CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Alkylamino", "alkenylthio", "alkenylsulfinyl", "alkenylsulfonyl", "alkynylthio", "alkynylsulfinyl", "alkynylsulfonyl", and the like, are defined analogously to the above examples. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2C(=O)$, $CH_3CH_2CH_2C(=O)$, $(CH_3)_2CHOC(=O)$ and the different butoxy- or pentoxycarbonyl isomers. "Cycloalkyl" includes, for example, cyclopropyl, cyclobutyl, cyclopentyl, and cyclohexyl. The term "cycloalkoxy" includes the same groups linked through an oxygen atom such as cyclopentyloxy and cyclohexyloxy. "Cycloalkylamino" means the amino nitrogen atom is attached to a cycloalkyl radical and a hydrogen atom and includes groups such as cyclopropylamino, cyclobutylamino, cyclopentylamino and cyclohexylamino. "(Alkyl)(cycloalkyl)amino" means a cycloalkylamino group where the hydrogen atom is replaced by an alkyl radical; examples include groups such as (methyl)(cyclopropyl)amino, (butyl)(cyclobutyl)amino, (propyl)cyclopentylamino, (methyl)cyclohexylamino and the like. "Cycloalkenyl" includes groups such as cyclopentenyl and cyclohexenyl as well as groups with more than one double bond such as 1,3- and 1,4-cyclohexadienyl.

The term "halogen", either alone or in compound words such as "haloalkyl", includes fluorine, chlorine, bromine or iodine. The term "1-2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$.

The total number of carbon atoms in a substituent group is indicated by the "$C_i$-$C_j$" prefix where i and j are, for example, numbers from 1 to 3; e.g., $C_1$-$C_3$ alkyl designates methyl through propyl.

Although there is no definite limit to the sizes of Formulae I and II suitable for the processes of the invention, typically Formula II comprises 4-100, more commonly 4-50, and most commonly 4-25 carbon atoms, and 3-25, more commonly 3-15, and most commonly 3-10 heteroatoms. The heteroatoms are commonly selected from halogen, oxygen, sulfur, nitrogen and phosphorus. Two heteroatoms in Formulae I and II are the dihydropyrazole ring nitrogen atoms; $X^1$ is halogen, and $X^2$ will contain at least one heteroatom.

Although there is no definite limit to the size of L and R (including $R^4$), optionally substituted alkyl moieties in L and R (including $R^4$) commonly include 1 to 6 carbon atoms, more commonly 1 to 4 carbon atoms and most commonly 1 to 2 carbon atoms in the alkyl chain. Optionally substituted alkenyl and alkynyl moieties in L and R (including $R^4$) commonly include 2 to 6 carbon atoms, more commonly 2 to 4 carbon atoms and most commonly 2 to 3 carbon atoms in the alkenyl or alkynyl chain.

Also, there is no definite limit to the size of the groups listed for $R^1$ and $R^2$ but alkyl, including derivatives such as alkoxy and haloalkyl, is commonly $C_1$-$C_6$, more commonly $C_1$-$C_4$, and most commonly $C_1$-$C_2$.

As indicated above, the carbon moieties L, R and $R^4$ may be (among others) an aromatic ring or ring system. Examples of aromatic rings or ring systems include a phenyl ring, 5- or 6-membered heteroaromatic rings aromatic 8-, 9- or 10-membered fused carbobicyclic ring systems and aromatic 8-, 9- or 10-membered fused heterobicyclic ring systems wherein each ring or ring system is optionally substituted. The term "optionally substituted" in connection with these L and R carbon moieties refers to carbon moieties which are unsubstituted or have at least one non-hydrogen substituent. These carbon moieties may be substituted with as many optional substituents as can be accommodated by replacing a hydrogen atom with a non-hydrogen substituent on any available carbon or nitrogen atom. Commonly, the number of optional substituents (when present) ranges from one to four. An example of phenyl optionally substituted with from one to four substituents is the ring illustrated as U-1 in Exhibit 1, wherein $R^v$ is any non-hydrogen substituent and r is an integer from 0 to 4. Examples of aromatic 8-, 9- or 10-membered fused carbobicyclic ring systems optionally substituted with from one to four substituents include a naphthyl group optionally substituted with from one to four substituents illustrated as U-85 and a 1,2,3,4-tetrahydronaphthyl group optionally substituted with from one to four substituents illustrated as U-86 in Exhibit 1, wherein $R^v$ is any substituent and r is an integer from 0 to 4. Examples of 5- or 6-membered heteroaromatic rings optionally substituted with from one to four substituents include the rings U-2 through U-53 illustrated in Exhibit 1 wherein $R^v$ is any substituent and r is an integer from 1 to 4. Examples of aromatic 8-, 9- or 10-membered fused heterobicyclic ring systems optionally substituted with from one to four substituents include U-54 through U-84 illustrated in Exhibit 1 wherein $R^v$ is any substituent and r is an integer from 0 to 4. Other examples of L and R include a benzyl group optionally substituted with from one to four substituents illustrated as U-87 and a benzoyl group optionally substituted with from one to four substituents illustrated as U-88 in Exhibit 1, wherein $R^v$ is any substituent and r is an integer from 0 to 4.

Although $R^v$ groups are shown in the structures U-1 through U-85, it is noted that they do not need to be present since they are optional substituents. The nitrogen atoms that require substitution to fill their valence are substituted with H or $R^v$. Note that some U groups can only be substituted with less than 4 $R^v$ groups (e.g. U-14, U-15, U-18 through U-21 and U-32 through U-34 can only be substituted with one $R^v$). Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formulae I and II through any available carbon of the U group by replacement of a hydrogen atom.

Exhibit 1

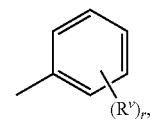

U-1

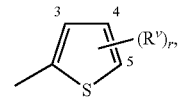

U-2

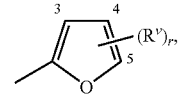

U-3

-continued
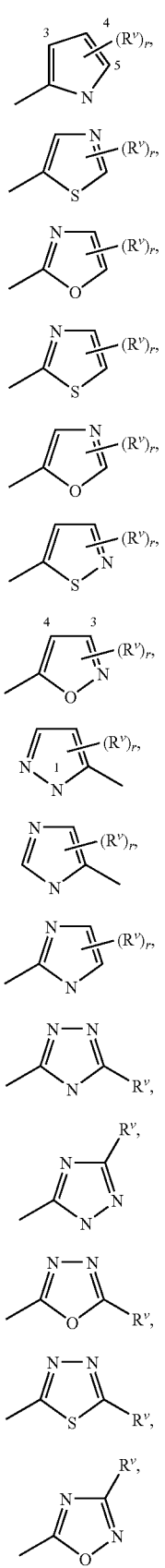
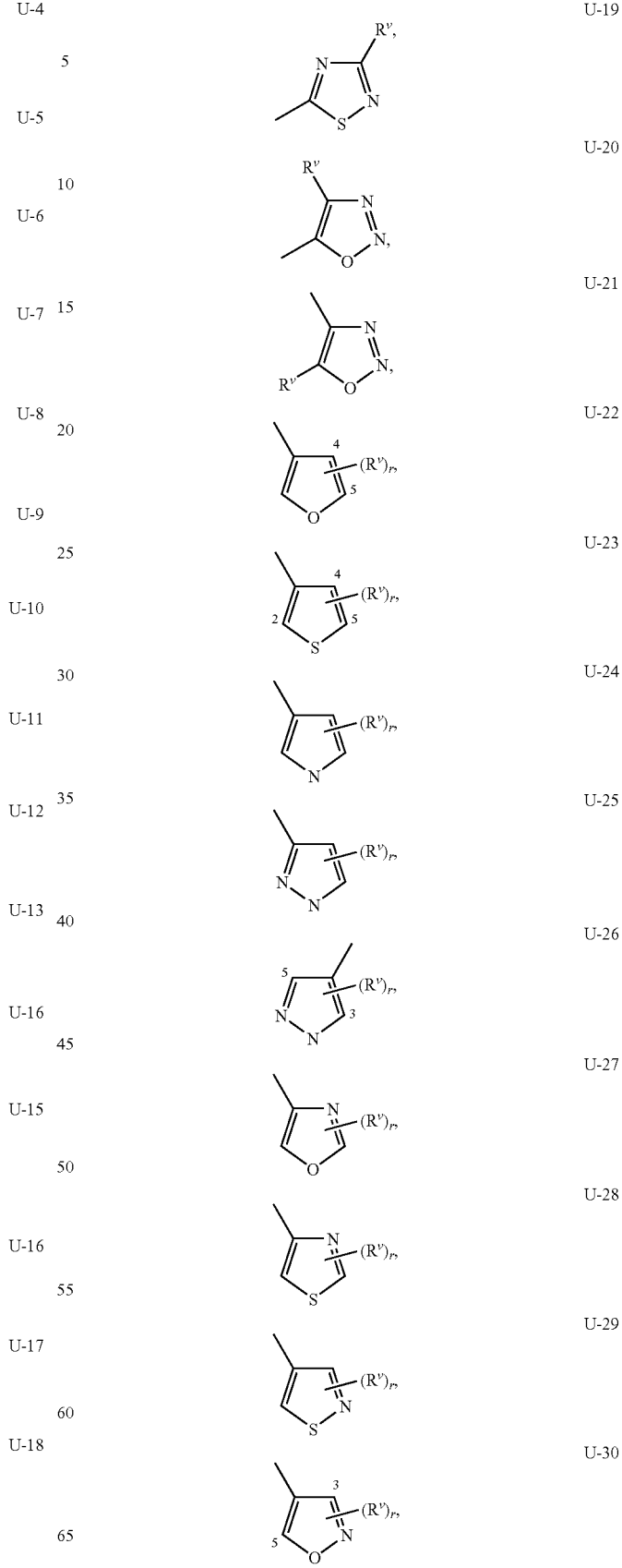
U-4
U-5
U-6
U-7
U-8
U-9
U-10
U-11
U-12
U-13
U-16
U-15
U-16
U-17
U-18
U-19
U-20
U-21
U-22
U-23
U-24
U-25
U-26
U-27
U-28
U-29
U-30

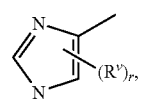 U-31
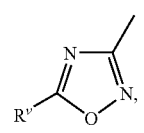 U-32
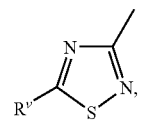 U-33
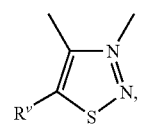 U-34
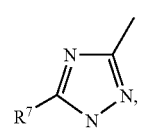 U-35
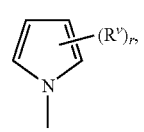 U-36
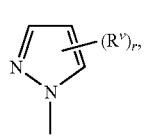 U-37
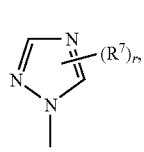 U-38
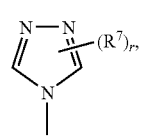 U-39
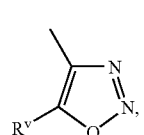 U-40
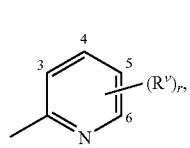 U-41
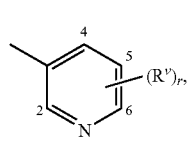 U-42
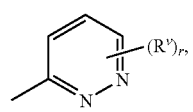 U-43
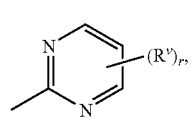 U-44
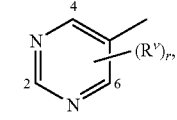 U-45
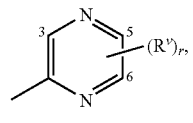 U-46
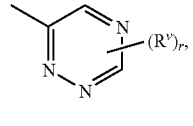 U-47
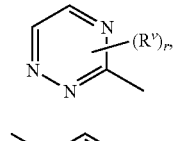 U-48
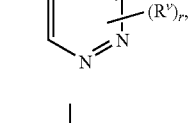 U-49
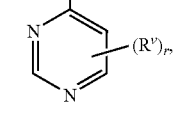 U-50
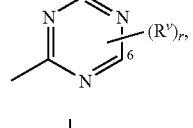 U-51
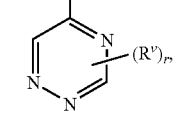 U-52
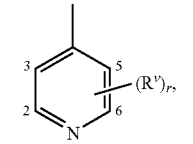 U-53
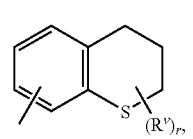 U-54

-continued
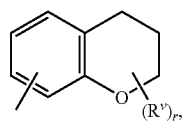 U-55
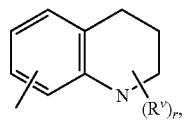 U-56
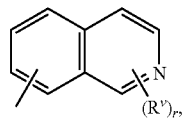 U-57
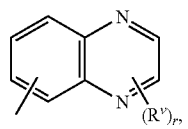 U-58
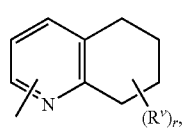 U-59
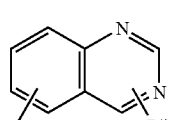 U-60
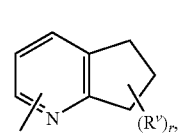 U-61
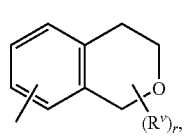 U-62
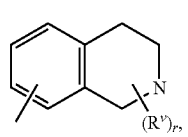 U-63
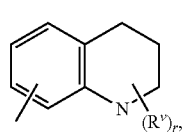 U-64
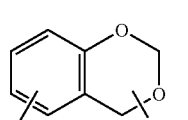 U-65
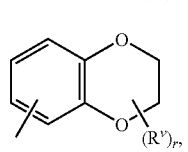 U-66
-continued
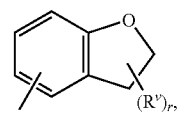 U-67
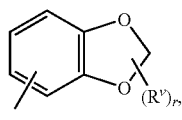 U-68
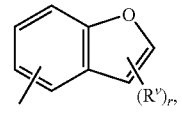 U-69
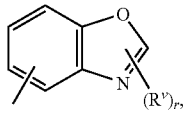 U-70
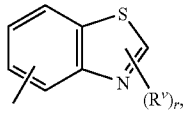 U-71
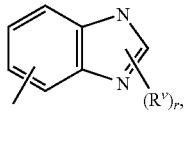 U-72
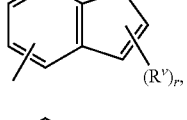 U-73
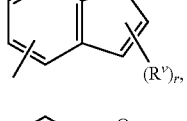 U-74
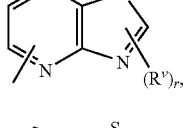 U-75
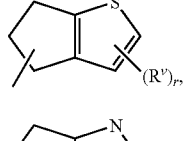 U-76
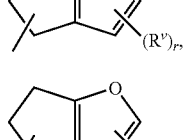 U-77
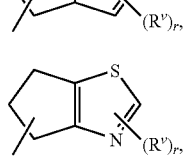 U-78
U-79

-continued

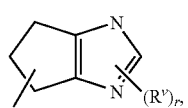
U-80

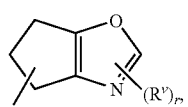
U-81

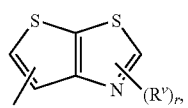
U-82

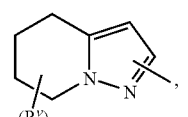
U-83

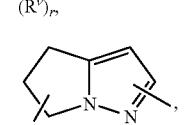
U-84

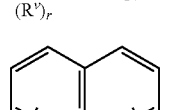
U-85

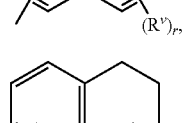
U-86

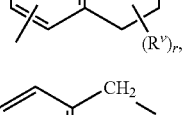
U-87 or

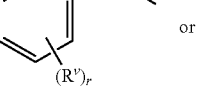
U-88

As indicated above, the carbon moieties L, R and $R^4$ may be (among others) saturated or partially saturated carbocyclic and heterocyclic rings, which can be further optionally substituted. The term "optionally substituted" in connection with these L and R carbon moieties refers to carbon moieties which are unsubstituted or have at least one non-hydrogen substituent. These carbon moieties may be substituted with as many optional substituents as can be accommodated by replacing a hydrogen atom with a non-hydrogen substituent on any available carbon or nitrogen atom. Commonly, the number of optional substituents (when present) ranges from one to four. Examples of saturated or partially saturated carbocyclic rings include optionally substituted $C_3$-$C_8$ cycloalkyl and optionally substituted $C_3$-$C_8$ cycloalkyl. Examples of saturated or partially saturated heterocyclic rings include 5- or 6-membered nonaromatic heterocyclic rings optionally including one or two ring members selected from the group consisting of C(=O), SO or S(O)$_2$, optionally substituted. Examples of such L and R carbon moieties include those illustrated as G-1 through G-35 in Exhibit 2. Note that when the attachment point on these G groups is illustrated as floating, the G group can be attached to the remainder of Formulae I and II through any available carbon or nitrogen of the G group by replacement of a hydrogen atom. The optional substituents can be attached to any available carbon or nitrogen by replacing a hydrogen atom (said substituents are not illustrated in Exhibit 2 since they are optional substituents). Note that when G comprises a ring selected from G-24 through G-31, G-34 and G-35, $Q^2$ may be selected from O, S, NH or substituted N.

Exhibit 2

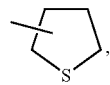
G-1

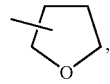
G-2

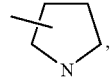
G-3

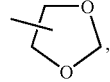
G-4

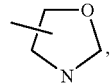
G-5

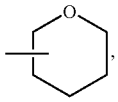
G-6

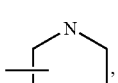
G-7

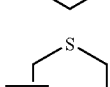
G-8

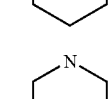
G-9

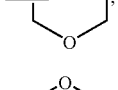
G-10

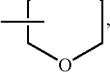
G-11

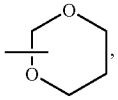
G-12

-continued

G-13 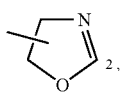

G-14 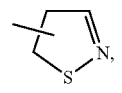

G-15 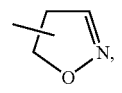

G-16 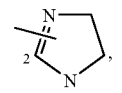

G-17 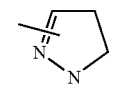

G-18 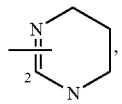

G-19 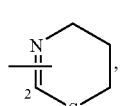

G-20 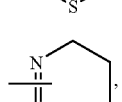

G-21 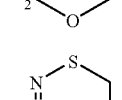

G-22 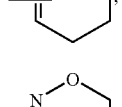

G-23 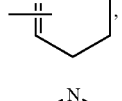

G-24 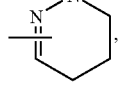

G-25 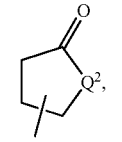

G-26 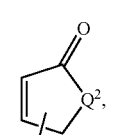

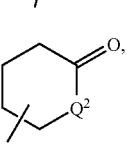

-continued

G-27 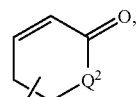

G-28 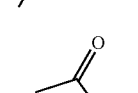

G-29 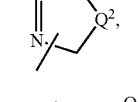

G-30 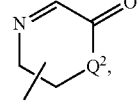

G-31 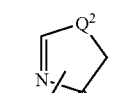

G-32 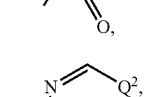

G-33 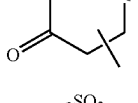

G-34 

and

G-35 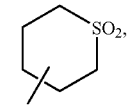

It is noted that the L, R and $R^4$ carbon moieties may be optionally substituted. As noted above, L and R carbon moieties may commonly comprise, among other groups, a U group or a G group further optionally substituted with from one to four substituents. Thus the L and R carbon moieties may comprise a U group or a G group selected from U-1 through U-88 or G-1 through G-35, and further substituted with additional substituents including one to four U or G groups (which may be the same or different) with both the core U or G group and substituent U or G groups optionally further substituted. Of particular note are L carbon moieties comprising a U group optionally substituted with from one to three additional substituents. For example, L can be the group U-41.

As shown in Scheme 1, according to the method of this invention a 4,5-dihydro-1H-pyrazole of Formula II in contacted with $HX^1$ to form a different 3-halo-4,5-dihydro-1H-pyrazole compound of Formula I.

Scheme 1

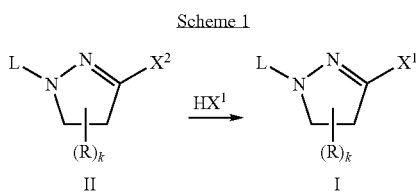

wherein L, R, $X^1$, $X^2$ and k are as defined in the Summary of the Invention.

The reaction is conducted in a suitable solvent. For best results the solvent should be non-nucleophilic, relatively inert to $HX^1$ and capable of dissolving the compound of Formula II. Suitable solvents include dibromomethane, dichloromethane, acetic acid, ethyl acetate and acetonitrile. The reaction can be conducted at or near atmospheric pressure or above atmospheric pressure in a pressure vessel. The $HX^1$ starting material can be added in the form of a gas to the reaction mixture containing the Formula II compound and solvent. When $X^2$ in the compound of Formula II is a halogen such as Cl, the reaction is preferably conducted in a way such that the $HX^2$ generated by the reaction is removed by sparging or other suitable means. Alternatively, the $HX^1$ starting material can be first dissolved in an inert solvent in which it is highly soluble (such as acetic acid) before contacting with the compound of Formula II either neat or in solution. Also when $X^2$ in the compound of Formula II is a halogen such as Cl, substantially more than one equivalent of $HX^1$ (e.g., 4 to 10 equivalents) is typically needed depending upon the level of conversion desired. One equivalent of $HX^1$ can provide high conversion when $X^2$ is $OS(O)_mR^1$ or $OP(O)_p(OR^2)_2$, but when the compound of Formula II comprises at least one basic function (e.g., a nitrogen-containing heterocycle), more than one equivalent is $HX^1$ is typically needed. The reaction can be conducted between about 0 and 100° C., most conveniently near ambient temperature (e.g., about 10-40° C.), and most preferably between about 20 and 30° C. Addition of a Lewis acid catalyst (e.g., aluminum bromide for preparing Formula I wherein $X^1$ is Br) can facilitate the reaction. The product of Formula I is isolated by the usual methods known to those skilled in the art, including extraction, distillation and crystallization.

For the method of this invention, preferred starting compounds include compounds of Formula II wherein m is 2 and p is 1. Also preferred are starting compounds of Formula II wherein $X^2$ is halogen or $OS(O)_mR^1$ (especially where m is 2). Further preferred are starting compounds of Formula II wherein $X^2$ is Cl or $OS(O)_mR^1$, m is 2, and $R^1$ is $C_{1-6}$ alkyl, $CF_3$ or phenyl optionally substituted with from 1 to 3 substituents selected from $C_1$-$C_4$ alkyl, and more preferably $R^1$ is $C_1$-$C_2$ alkyl, phenyl or 4-methylphenyl. Particularly preferred methods of this invention include those using a starting compound of Formula II wherein $X^2$ is Cl or $OS(O)_2R^1$, and $R^1$ is methyl, phenyl or 4-methylphenyl. Especially preferred method of this invention include those using a starting compound of Formula II wherein $X^2$ is Cl or $OS(O)_2R^1$, and $R^1$ is phenyl or 4-methylphenyl.

For the method of this invention, preferred product compounds include compounds of Formula I wherein $X^1$ is Cl, Br or I. More preferred product compounds include compounds of Formula I wherein $X^1$ is Cl or Br. Most preferred product compounds include compounds of Formula I wherein $X^1$ is Br. Particularly useful embodiments of the method of this invention include the preparation of a compound of Formula I wherein $X^1$ is Cl or Br from a compound of Formula II wherein $X^2$ is $OS(O)_2R^1$, wherein $R^1$ is, for example, methyl, phenyl or 4-methylphenyl, more preferably phenyl or 4-methylphenyl.

Preferred methods of this invention include the method wherein the starting compound of Formula II is Formula Ia and the product compound of Formula I is Formula Ia as shown in Scheme 2 below.

Scheme 2

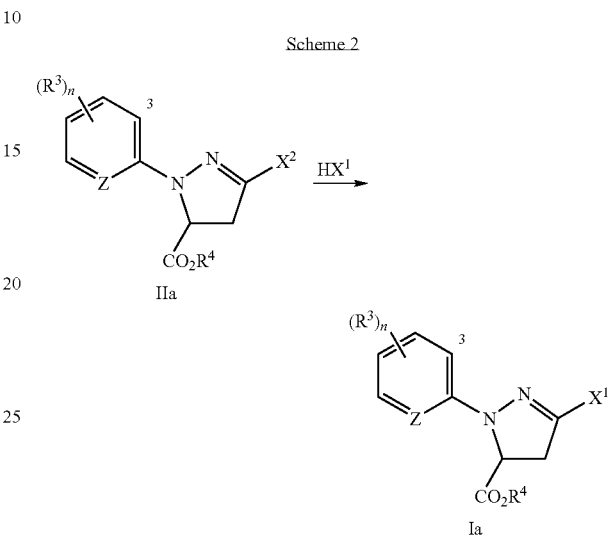

wherein $X^1$ and $X^2$ are as defined for Formulae I and II;

each $R^3$ is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_{1-4}$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $(C_1$-$C_4$ alkyl)($C_3$-$C_6$ cycloalkyl)amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

$R^4$ is H or an optionally substituted carbon moiety;

Z is N or $CR^5$;

$R^5$ is H or $R^3$; and n is an integer selected from 0 to 3.

One skilled in the art will recognize that Formula Ia is a subgenus of Formula I, and Formula IIa is subgenus of Formula II.

While a wide range of optionally substituted carbon moieties as already described are useful as $R^4$ in esters of Formula Ia for the method of Scheme 2, commonly $R^4$ is a radical containing up to 18 carbon atoms and selected from alkyl, alkenyl and alkynyl; and benzyl and phenyl, each optionally substituted with alkyl and halogen. Most preferably $R^4$ is $C_1$-$C_4$ alkyl.

Of note is the method shown in Scheme 2 wherein Z is N, n is 1 and $R^3$ is Cl or Br and is located at the 3-position. Also of note is the method shown in Scheme 2 wherein $X^2$ is halogen or $OS(O)_2R^1$, particularly where $R^1$ is methyl, phenyl or 4-methylphenyl. Also of note is the method shown in Scheme 2 wherein $X^1$ is Br or Cl and more particularly $X^1$ is Br. Of particular note is the method shown in Scheme 2 wherein $X^1$ is Br, $X^2$ is Cl or $OS(O)_mR^1$, m is 2, and $R^1$ is phenyl or 4-methylphenyl.

When a basic functionality is present in the compound of Formula IIa (e.g., Z is N and/or $R^3$ is alkylamino, dialkylamino, cycloalkylamino or (alkyl)(cycloalkyl)amino) typically more than one equivalent of $HX^1$ is needed for satisfactory conversion even when $X^2$ is $OS(O)_mR^1$ or $OP(O)_p(OR^2)_2$. When Z is N, $R^3$ is other than alkylamino, dialkylamino, cycloalkylamino and (alkyl)(cycloalkyl)amino), and $X^2$ is $S(O)_2R^1$ in Formula IIa, excellent conversion is obtained using as little as 1.5 to 2 equivalents of $HX^1$.

Starting compounds of Formula II wherein $X^2$ is halogen can be prepared from corresponding compounds of Formula 1 as shown in Scheme 3

Scheme 3

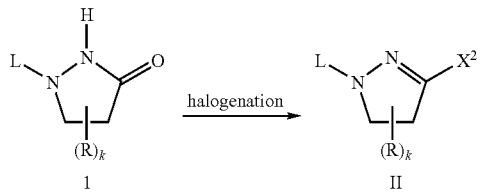

wherein $X^2$ is halogen and L, R and k are as previously defined.

Treatment of a compound of Formula 1 with a halogenating reagent, usually in the presence of a solvent, affords the corresponding halo compound of Formula II. Halogenating reagents that can be used include phosphorus oxyhalides, phosphorus trihalides, phosphorus pentahalides, thionyl chloride, dihalotrialkylphosphoranes, dihalodiphenylphosphoranes, oxalyl chloride, phosgene, sulfur tetrafluoride and (diethylamino)sulfur trifluoride. Preferred are phosphorus oxyhalides and phosphorus pentahalides. To obtain complete conversion, at least 0.33 equivalents of phosphorus oxyhalide versus the compound of Formula 1 (i.e. the mole ratio of phosphorus oxyhalide to Formula 1 is at least 0.33) should be used, preferably between about 0.33 and 1.2 equivalents. To obtain complete conversion, at least 0.20 equivalents of phosphorus pentahalide versus the compound of Formula 1 should be used, preferably between about 0.20 and 1.0 equivalents. Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option. Preferred is the process in which the solvent is acetonitrile and a base is absent. Typically, neither a base nor a catalyst is required when acetonitrile solvent is used. The preferred process is conducted by mixing the compound of Formula 1 in acetonitrile. The halogenating reagent is then added over a convenient time, and the mixture is then held at the desired temperature until the reaction is complete. The reaction temperature is typically between about 20° C. and the boiling point of acetonitrile, and the reaction time is typically less than 2 hours. The reaction mass is then neutralized with an inorganic base, such as sodium bicarbonate, sodium hydroxide and the like, or an organic base, such as sodium acetate. The desired product, a compound of Formula II, can be isolated by methods known to those skilled in the art, including extraction, crystallization and distillation.

As shown in Scheme 4, starting compounds of Formula II wherein $R^1$ is a $OS(O)_mR^1$, or $OP(O)_p(OR^2)_2$ can likewise be prepared from corresponding compounds of Formula 1 by contacting with $X^3S(O)_mR^1$ (2) or $X^3P(O)_p(OR^2)_2$ (3), respectively, wherein $X^3$ is a nucleophilic reaction leaving group. Halides such as Cl are particularly useful for $X^3$. Also useful for $X^3S(O)_mR^1$ is $X^3$ being $OS(O)_mR^1$ (i.e. Formula 2 is $R^1S(O)_mOS(O)_mR^1$); $X^3$ being $OS(O)_mR^1$ is particularly useful when $R^1$ is $CF_3$. In view of synthetic accessibility and relatively low cost, $X^3$ being Cl is generally preferred.

Scheme 4

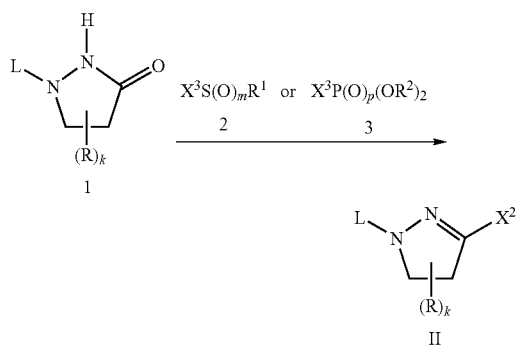

wherein $X^2$ is $OS(O)_mR^1$ or $OP(O)_p(OR^2)_2$, $X^3$ is a leaving group, and L, R, $R^1$, k, m and p are as previously defined.

In this method, the compound of Formula 1 is contacted with a compound of Formula 2 (for $X^2$ being $OS(O)_mR^1$) or Formula 3 (for $X^2$ being $OP(O)_p(OR^2)_2$), typically in the presence of a solvent and a base. Suitable solvents include dichloromethane, tetrahydrofuran, acetonitrile and the like. Suitable bases include tertiary amines (e.g., triethylamine, N,N-diisopropylethylamine) and ionic bases such as potassium carbonate and the like. A tertiary amine is preferred as the base. At least one of equivalent (preferably a small excess, e.g., 5-10%) of the compound of Formula 2 or Formula 3 and the base relative to the compound Formula 1 is generally used to give complete conversion. The reaction is typically conducted at a temperature between about −50° C. and the boiling point of the solvent, more commonly between about 0° C. and ambient temperature (i.e. about 15 to 30° C.). The reaction is typically complete within a couple hours to several days; the progress of the reaction can by monitored by such techniques known to those skilled in the art as thin layer chromatography and analysis of the $^1H$ NMR spectrum. The reaction mixture is then worked up, such as by washing with water, drying the organic phase and evaporating the solvent. The desired product, a compound of Formula II, can be isolated by methods known to those skilled in the art, including extraction, crystallization and distillation.

As Formula IIa is a subgenus of Formula II, compounds of Formula IIa can be prepared from corresponding compounds of Formula 1a, which is a subgenus of Formula 1, by the methods already described for Schemes 3 and 4.

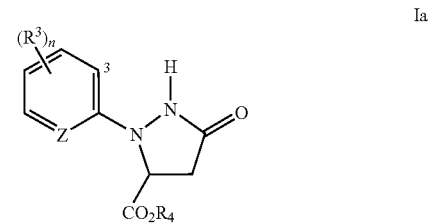

Ia wherein $R^3$, $R^4$, Z and n are as defined for Formula IIa.

Compounds of Formula 1 can be prepared by the great variety of modern synthetic methodologies known to those skilled in the art. For example, compounds of Formula 1a can be prepared from compounds of Formulae 4 and 5 as outlined in Scheme 5.

Scheme 5

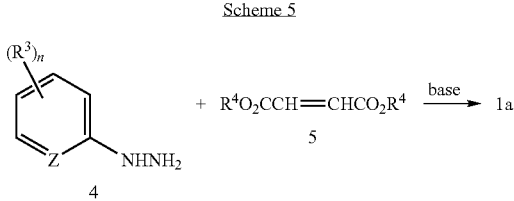

wherein $R^3$, $R^4$, Z and N are as Defined for Formula IIa.

In this method, a hydrazine compound of Formula 4 is contacted with a compound of Formula 5 (a fumarate ester or maleate ester or a mixture thereof may be used) in the presence of a base and a solvent. The base is typically a metal alkoxide salt, such as sodium methoxide, potassium methoxide, sodium ethoxide, potassium ethoxide, potassium tert-butoxide, lithium tert-butoxide, and the like. Greater than 0.5 equivalents of base versus the compound of Formula 4 should be used, preferably between 0.9 and 1.3 equivalents. Greater than 1.0 equivalents of the compound of Formula 5 should be used, preferably between 1.0 to 1.3 equivalents. Polar protic and polar aprotic organic solvents can be used, such as alcohols, acetonitrile, tetrahydrofuran, N,N-dimethylformamide, dimethyl sulfoxide and the like. Preferred solvents are alcohols such as methanol and ethanol. It is especially preferred that the alcohol be the same as that making up the fumarate or maleate ester and the alkoxide base. The reaction is typically conducted by mixing the compound of Formula 4 and the base in the solvent. The mixture can be heated or cooled to a desired temperature and the compound of Formula 5 added over a period of time. Typically reaction temperatures are between 0° C. and the boiling point of the solvent used. The reaction may be conducted under greater than atmospheric pressure in order to increase the boiling point of the solvent. Temperatures between about 30 and 90° C. are generally preferred. The addition time can be as quick as heat transfer allows. Typical addition times are between 1 minute and 2 hours. Optimum reaction temperature and addition time vary depending upon the identities of the compounds of Formula 4 and Formula 5. After addition, the reaction mixture can be held for a time at the reaction temperature. Depending upon the reaction temperature, the required hold time may be from 0 to 2 hours. Typical hold times are 10 to 60 minutes. The reaction mass then can be acidified by adding an organic acid, such as acetic acid and the like, or an inorganic acid, such as hydrochloric acid, sulfuric acid and the like. Depending on the reaction conditions and the means of isolation, the —$CO_2R^4$ function on the compound of Formula 1a may be hydrolyzed to —$CO_2H$; for example, the presence of water in the reaction mixture can promote such hydrolysis. If the carboxylic acid (—$CO_2H$) is formed, it can be converted back to —$CO_2R^4$ wherein $R^4$ is, for example, $C_1$-$C_4$ alkyl using esterification methods well-known in the art. The desired product, a compound of Formula 1a, can be isolated by methods known to those skilled in the art, such as crystallization, extraction or distillation.

It is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet.

Example 1

Preparation of ethyl 3-bromo-1-(3-chloro-2-pyridinyl)-4,5-dihydro-1H-pyrazole-5-carboxylate by replacement of chlorine with bromine Step A: Preparation of ethyl 2-(3-chloro-2-pyridinyl)-5-oxo-3-pyrazolidine-carboxylate A 2-L four-necked flask equipped with a mechanical stirrer, thermometer, addition funnel, reflux condenser, and nitrogen inlet was charged with absolute ethanol (250 mL) and an ethanolic solution of sodium ethoxide (21%, 190 mL, 0.504 mol). The mixture was heated to reflux at about 83° C. It was then treated with 3-chloro-2(1H)-pyridinone hydrazone (68.0 g, 0.474 mol). The mixture was re-heated to reflux over a period of 5 minutes. The yellow slurry was then treated dropwise with diethyl maleate (88.0 mL, 0.544 mol) over a period of 5 minutes. The reflux rate increased markedly during the addition. By the end of the addition all of the starting material had dissolved. The resulting orange-red solution was held at reflux for 10 minutes. After being cooled to 65° C., the reaction mixture was treated with glacial acetic acid (50.0 mL, 0.873 mol). A precipitate formed. The mixture was diluted with water (650 mL), causing the precipitate to dissolve. The orange solution was cooled in an ice bath. Product began to precipitate at 28° C. The slurry was held at about 2° C. for 2 hours. The product was isolated via filtration, washed with aqueous ethanol (40%, 3×50 mL), and then air-dried on the filter for about 1 hour. The title product compound was obtained as a highly crystalline, light orange powder (70.3 g, 55% yield). No significant impurities were observed by $^1$H NMR.

$^1$H NMR (DMSO-$d_6$) δ 1.22 (t, 3H), 2.35 (d, 1H), 2.91 (dd, 1H), 4.20 (q, 2H), 4.84 (d, 1H), 7.20 (dd, 1H), 7.92 (d, 1H), 8.27 (d, 1H), 10.18 (s, 1H).

Step B: Preparation of ethyl 3-chloro-1-(3-chloro-2-pyridinyl)-4,5-dihydro-1H-pyrazole-5-carboxylate To a 2-L four-necked flask equipped with a mechanical stirrer, thermometer, reflux condenser, and nitrogen inlet was charged acetonitrile (1000 mL), ethyl 2-(3-chloro-2-pyridinyl)-5-oxo-3-pyrazolidinecarboxylate (i.e. the product of Step A) (91.0 g, 0.337 mol) and phosphorus oxychloride (35.0 mL, 0.375 mol). Upon adding the phosphorus oxychloride, the mixture self-heated from 22 to 25° C. and a precipitate formed. The light-yellow slurry was heated to reflux at 83° C. over a period of 35 minutes, whereupon the precipitate dissolved. The resulting orange solution was held at reflux for 45 minutes, whereupon it had become black-green. The reflux condenser was replaced with a distillation head, and 650 mL of solvent was removed by distillation. A second 2-L four-necked flask equipped with a mechanical stirrer was charged with sodium bicarbonate (130 g, 1.55 mol) and water (400 mL). The concentrated reaction mixture was added to the sodium bicarbonate slurry over a period of 15 minutes.

The resulting, two-phase mixture was stirred vigorously for 20 minutes, at which time gas evolution had ceased. The mixture was diluted with dichloromethane (250 mL) and then was stirred for 50 minutes. The mixture was treated with Celite® 545 diatomaceous earth filter aid (11 g) and then filtered to remove a black, tarry substance that inhibited phase separation. Since the filtrate was slow to separate into distinct phases, it was diluted with dichloromethane (200 mL) and water (200 mL) and treated with more Celite® 545 (15 g). The mixture was filtered, and the filtrate was transferred to a separatory funnel. The heavier, deep green organic layer was separated. A rag layer (50 mL) was refiltered and then added to the organic layer. The organic solution (800 mL) was treated with magnesium sulfate (30 g) and silica gel (12 g), and the slurry was stirred magnetically for 30 minutes. The slurry was filtered to remove the magnesium sulfate and silica gel, which had become deep blue-green. The filter cake was washed with dichloromethane (100 mL). The filtrate was concentrated on a rotary evaporator. The product consisted of dark amber oil (92.0 g, 93% yield). The only appreciable impurities observed by $^1$H NMR were 1% starting material and 0.7% acetonitrile.

$^1$H NMR (DMSO-$d_6$) δ 1.15 (t, 3H), 3.26 (dd, 1H), 3.58 (dd, 1H), 4.11 (q, 2H), 5.25 (dd, 1H), 7.00 (dd, 1H), 7.84 (d, 1H), 8.12 (d, 1H).

Step C: Preparation of ethyl 3-bromo-1-(3-chloro-2-pyridinyl)-4,5-dihydro-1H-pyrazole-5-carboxylate Hydrogen bromide was passed through a solution of ethyl 3-chloro-1-(3-chloro-2-pyridinyl)-4,5-dihydro-1H-pyrazole-5-carboxylate (i.e. product of Step B) (8.45 g, 29.3 mmol) in dibromomethane (85 mL). After 90 minutes the gas flow was terminated, and the reaction mixture was washed with aqueous sodium bicarbonate solution (100 mL). The organic phase was dried and evaporated under reduced pressure to give the title product as an oil (9.7 g, 99% yield), which crystallized on standing.

$^1$H NMR (CDCl$_3$) δ 1.19 (t, 3H), 3.24 (½ of AB in ABX pattern, J=9.3, 17.3 Hz, 1H), 3.44 (½ of AB in ABX pattern, J=11.7, 17.3 Hz, 1H), 4.18 (q, 2H), 5.25 (X of ABX, 1H, J=9.3, 11.9 Hz), 6.85 (dd, J=4.7, 7.7 Hz, 1H), 7.65 (dd, J=1.6, 7.8 Hz, 1H), 8.07 (dd, J=1.6, 4.8 Hz, 1H).

Example 2

Preparation of ethyl 3-bromo-1-(3-chloro-2-pyridinyl)-4,5-dihydro-1H-pyrazole-5-carboxylate by replacement of tosylate with bromine Step A: Preparation of ethyl 1-(3-chloro-2-pyridinyl)-4,5-dihydro-3-[[(4-methyl-phenyl)sulfonyl]oxy]-1H-pyrazole-5-carboxylate Triethylamine (3.75 g, 37.1 mmol) was added dropwise to a mixture of ethyl 2-(3-chloro-2-pyridinyl)-5-oxo-3-pyrazolidinecarboxylate (i.e. the product of Example 1, Step A) (10.0 g, 37.1 mmol) and p-toluenesulfonyl chloride (7.07 g, 37.1 mmol) in dichloromethane (100 mL) at 0° C. Further portions of p-toluenesulfonyl chloride (0.35 g, 1.83 mmol) and triethylamine (0.19 g, 1.88 mmol) were added. The reaction mixture was then allowed to warm to room temperature and was stirred overnight. The mixture was then diluted with dichloromethane (200 mL) and washed with water (3×70 mL). The organic phase was dried and evaporated to leave the title product as an oil (13.7 g, 87% yield), which slowly formed crystals. Product recrystallized from ethyl acetate/hexanes melted at 99.5-100° C.

IR (nujol): 1740, 1638, 1576, 1446, 1343, 1296, 1228, 1191, 1178, 1084, 1027, 948, 969, 868, 845 cm$^{-1}$.

$^1$H NMR (CDCl$_3$) δ 1.19 (t, 3H), 2.45 (s, 3H), 3.12 (½ of AB in ABX pattern, J=17.3, 9 Hz, 1H), 3.33 (½ of AB in ABX pattern, J=17.5, 11.8 Hz, 1H), 4.16 (q, 2H), 5.72 (X of ABX, J=9, 11.8 Hz, 1H), 6.79 (dd, J=4.6, 7.7 Hz, 1H), 7.36 (d, J=8.4 Hz, 2H), 7.56 (dd, J=1.6, 7.8 Hz, 1H), 7.95 (d, J=8.4 Hz, 2H), 8.01 (dd, J=1.4, 4.6 Hz, 1H).

Step B: Preparation of ethyl 3-bromo-1-(3-chloro-2-pyridinyl)-4,5-dihydro-1H-pyrazole-5-carboxylate Hydrogen bromide was passed through a solution of ethyl 1-(3-chloro-2-pyridinyl)-4,5-dihydro-3-[[(4-methylphenyl)sulfonyl]oxy]-1H-pyrazole-5-carboxylate (i.e. product of Step A) (5 g, 11.8 mmol) in dibromomethane (50 mL). After about 60 minutes the gas flow was terminated, and the reaction mixture was washed with aqueous sodium bicarbonate solution (50 mL). The organic phase was dried and evaporated under reduced pressure to give the title product as an oil (3.92 g, 100% yield), which crystallized on standing. The $^1$H NMR spectrum of the product was the same as reported for the product of Example 1, Step C.

Example 3

Preparation of ethyl 3-bromo-1-(3-chloro-2-pyridinyl)-4,5-dihydro-1H-pyrazole-5-carboxylate by replacement of benzenesulfonate with bromine Step A: Preparation of ethyl 1-(3-chloro-2-pyridinyl)-4,5-dihydro-3-[(phenyl-sulfonyl)oxy]-1H-pyrazole-5-carboxylate Triethylamine (1.85 g, 18.5 mmol) was added dropwise over 1 h to a mixture of ethyl 2-(3-chloro-2-pyridinyl)-5-oxo-3-pyrazolidinecarboxylate (i.e. the product of Example 1, Step A) (5.0 g, 18.5 mmol) and benzenesulfonyl chloride (3.27 g, 18.5 mmol) in dichloromethane (20 mL) at 0° C. The temperature was not allowed to exceed 1° C. After stirring the reaction mixture for an additional 2 h, a further portion of benzenesulfonyl chloride (0.5 g, 1.85 mmol) was added. Then a further portion of triethylamine (0.187 g, 1.85 mmol) was added dropwise to the mixture. After stirring for 0.5 h more, the mixture was partitioned between water (100 mL) and dichloromethane (100 mL). The organic layer was dried (MgSO$_4$) and evaporated to provide the title product as an orange solid (7.18 g, 94% yield). Product recrystallized from ethyl acetate/hexanes melted at 84-85° C.

IR (nujol): 1737, 1639, 1576, 1448, 1385, 1346, 1302, 1233, 1211, 1188, 1176, 1088, 1032, 944, 910, 868, 846 cm$^{-1}$.

$^1$H NMR (CDCl$_3$) δ 1.19 (t, 3H), 3.15 (½ of the AB in ABX pattern, J=8.8, 17.3 Hz, 1H), 3.36 (½ of the AB in ABX pattern, J=11.8, 17.3 Hz, 1H), 4.17 (q, 2H), 5.23 (X of ABX, J=8.8, 11.8 Hz, 1H), 6.78 (dd, J=2.8, 4.8 Hz, 1H), 7.71-7.55 (m, 4H), 8.01 (dd, J=1.6, 4.6 Hz, 2H), 8.08 (dd, J=1.0, 2.6 Hz, 2H).

Step B: Preparation of ethyl 3-bromo-1-(3-chloro-2-pyridinyl)-4,5-dihydro-1H-pyrazole-5-carboxylate A solution of ethyl 1-(3-chloro-2-pyridinyl)-4,5-dihydro-3-[(phenylsulfonyl)oxy]-1H-pyrazole-5-carboxylate (i.e. the product of Step A) (1.0 g, 2.44 mmol) in acetic acid (4 mL) was added to a solution of hydrogen bromide in acetic acid (33%, 1.2 g, 4.89 mmol). After about 1 h the reaction mixture was added to saturated aqueous sodium hydrogen carbonate solution (100 mL). The mixture was then extracted with ethyl acetate (2×50 mL), and the combined extracts were dried (MgSO$_4$) and evaporated to provide the title product as an oil (0.69 g, 85% yield), which slowly crystallized. The $^1$H NMR spectrum was the same as reported for the product of Example 1, Step C.

By the procedures described herein together with methods known in the art, the compounds of Formula II can be converted to compounds of Formula I as illustrated for Formulae Ia and IIa in Table 1. The following abbreviations are used in the Table: t is tertiary, s is secondary, n is normal, i is iso, Me is methyl, Et is ethyl, Pr is propyl, i-Pr is isopropyl, t-Bu is tertiary butyl and Ph is phenyl.

TABLE 1

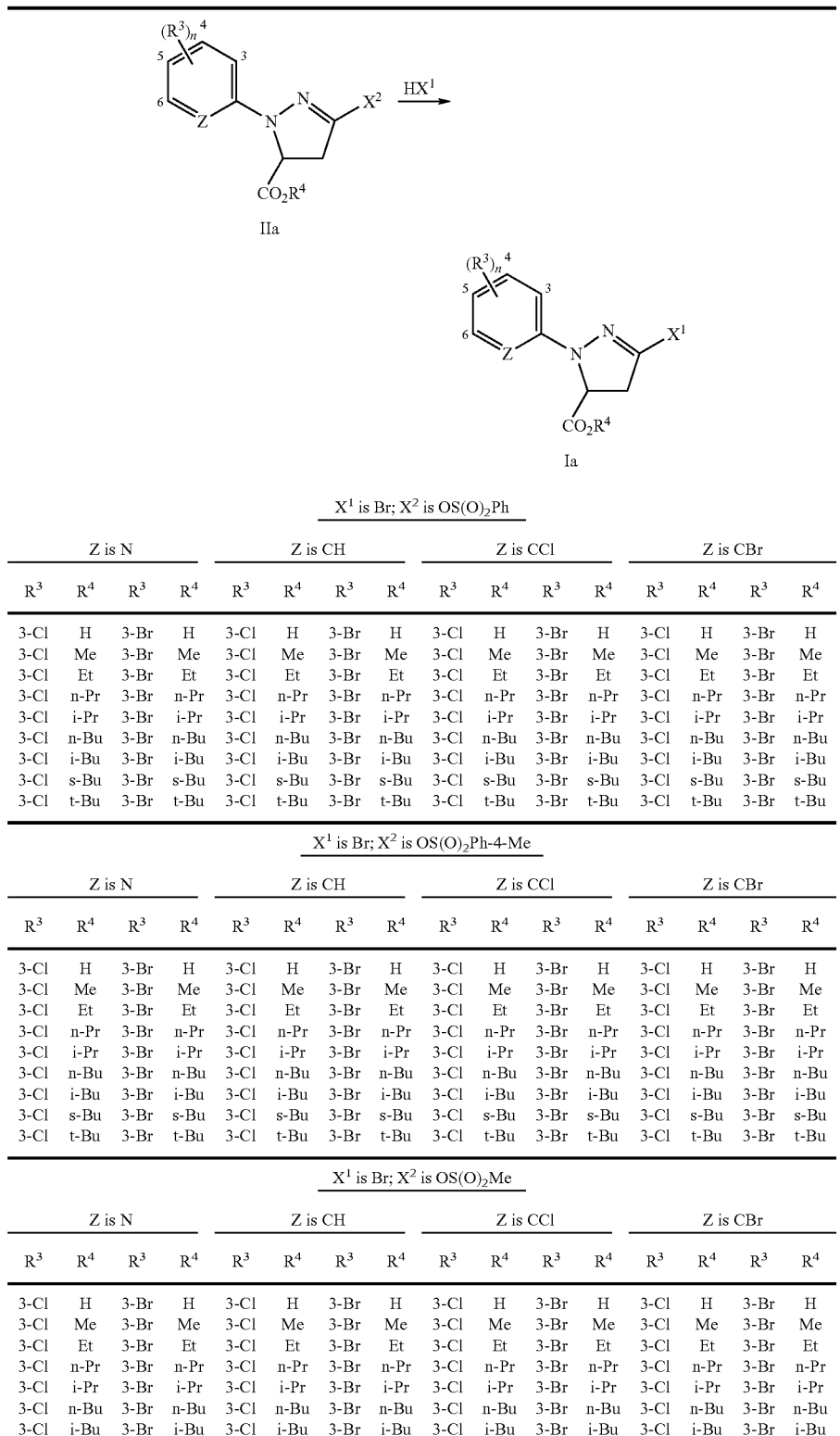

$X^1$ is Br; $X^2$ is $OS(O)_2Ph$

| Z is N | | Z is CH | | Z is CCl | | Z is CBr | |
|---|---|---|---|---|---|---|---|
| $R^3$ | $R^4$ | $R^3$ | $R^4$ | $R^3$ | $R^4$ | $R^3$ | $R^4$ |
| 3-Cl | H | 3-Br | H | 3-Cl | H | 3-Br | H |
| 3-Cl | Me | 3-Br | Me | 3-Cl | Me | 3-Br | Me |
| 3-Cl | Et | 3-Br | Et | 3-Cl | Et | 3-Br | Et |
| 3-Cl | n-Pr | 3-Br | n-Pr | 3-Cl | n-Pr | 3-Br | n-Pr |
| 3-Cl | i-Pr | 3-Br | i-Pr | 3-Cl | i-Pr | 3-Br | i-Pr |
| 3-Cl | n-Bu | 3-Br | n-Bu | 3-Cl | n-Bu | 3-Br | n-Bu |
| 3-Cl | i-Bu | 3-Br | i-Bu | 3-Cl | i-Bu | 3-Br | i-Bu |
| 3-Cl | s-Bu | 3-Br | s-Bu | 3-Cl | s-Bu | 3-Br | s-Bu |
| 3-Cl | t-Bu | 3-Br | t-Bu | 3-Cl | t-Bu | 3-Br | t-Bu |

(Note: the above block repeats for Z is CCl and Z is CBr with the same R³/R⁴ values)

$X^1$ is Br; $X^2$ is $OS(O)_2Ph$-4-Me

| Z is N | | Z is CH | | Z is CCl | | Z is CBr | |
|---|---|---|---|---|---|---|---|
| $R^3$ | $R^4$ | $R^3$ | $R^4$ | $R^3$ | $R^4$ | $R^3$ | $R^4$ |
| 3-Cl | H | 3-Br | H | 3-Cl | H | 3-Br | H |
| 3-Cl | Me | 3-Br | Me | 3-Cl | Me | 3-Br | Me |
| 3-Cl | Et | 3-Br | Et | 3-Cl | Et | 3-Br | Et |
| 3-Cl | n-Pr | 3-Br | n-Pr | 3-Cl | n-Pr | 3-Br | n-Pr |
| 3-Cl | i-Pr | 3-Br | i-Pr | 3-Cl | i-Pr | 3-Br | i-Pr |
| 3-Cl | n-Bu | 3-Br | n-Bu | 3-Cl | n-Bu | 3-Br | n-Bu |
| 3-Cl | i-Bu | 3-Br | i-Bu | 3-Cl | i-Bu | 3-Br | i-Bu |
| 3-Cl | s-Bu | 3-Br | s-Bu | 3-Cl | s-Bu | 3-Br | s-Bu |
| 3-Cl | t-Bu | 3-Br | t-Bu | 3-Cl | t-Bu | 3-Br | t-Bu |

$X^1$ is Br; $X^2$ is $OS(O)_2Me$

| Z is N | | Z is CH | | Z is CCl | | Z is CBr | |
|---|---|---|---|---|---|---|---|
| $R^3$ | $R^4$ | $R^3$ | $R^4$ | $R^3$ | $R^4$ | $R^3$ | $R^4$ |
| 3-Cl | H | 3-Br | H | 3-Cl | H | 3-Br | H |
| 3-Cl | Me | 3-Br | Me | 3-Cl | Me | 3-Br | Me |
| 3-Cl | Et | 3-Br | Et | 3-Cl | Et | 3-Br | Et |
| 3-Cl | n-Pr | 3-Br | n-Pr | 3-Cl | n-Pr | 3-Br | n-Pr |
| 3-Cl | i-Pr | 3-Br | i-Pr | 3-Cl | i-Pr | 3-Br | i-Pr |
| 3-Cl | n-Bu | 3-Br | n-Bu | 3-Cl | n-Bu | 3-Br | n-Bu |
| 3-Cl | i-Bu | 3-Br | i-Bu | 3-Cl | i-Bu | 3-Br | i-Bu |

TABLE 1-continued

| 3-Cl | s-Bu | 3-Br | s-Bu | 3-Cl | s-Bu | 3-Br | s-Bu | 3-Cl | s-Bu | 3-Br | s-Bu | 3-Cl | s-Bu | 3-Br | s-Bu |
| 3-Cl | t-Bu | 3-Br | t-Bu | 3-Cl | t-Bu | 3-Br | t-Bu | 3-Cl | t-Bu | 3-Br | t-Bu | 3-Cl | t-Bu | 3-Br | t-Bu |

$X^1$ is Br; $X^2$ is Cl

| Z is N | | | | Z is CH | | | | Z is CCl | | | | Z is CBr | | | |
|---|---|---|---|---|---|---|---|---|---|---|---|---|---|---|---|
| $R^3$ | $R^4$ | $R^3$ | $R^4$ | $R^3$ | $R^4$ | $R^3$ | $R^4$ | $R^3$ | $R^4$ | $R^3$ | $R^4$ | $R^3$ | $R^4$ | $R^3$ | $R^4$ |
| 3-Cl | H | 3-Br | H | 3-Cl | H | 3-Br | H | 3-Cl | H | 3-Br | H | 3-Cl | H | 3-Br | H |
| 3-Cl | Me | 3-Br | Me | 3-Cl | Me | 3-Br | Me | 3-Cl | Me | 3-Br | Me | 3-Cl | Me | 3-Br | Me |
| 3-Cl | Et | 3-Br | Et | 3-Cl | Et | 3-Br | Et | 3-Cl | Et | 3-Br | Et | 3-Cl | Et | 3-Br | Et |
| 3-Cl | n-Pr | 3-Br | n-Pr | 3-Cl | n-Pr | 3-Br | n-Pr | 3-Cl | n-Pr | 3-Br | n-Pr | 3-Cl | n-Pr | 3-Br | n-Pr |
| 3-Cl | i-Pr | 3-Br | i-Pr | 3-Cl | i-Pr | 3-Br | i-Pr | 3-Cl | i-Pr | 3-Br | i-Pr | 3-Cl | i-Pr | 3-Br | i-Pr |
| 3-Cl | n-Bu | 3-Br | n-Bu | 3-Cl | n-Bu | 3-Br | n-Bu | 3-Cl | n-Bu | 3-Br | n-Bu | 3-Cl | n-Bu | 3-Br | n-Bu |
| 3-Cl | i-Bu | 3-Br | i-Bu | 3-Cl | i-Bu | 3-Br | i-Bu | 3-Cl | i-Bu | 3-Br | i-Bu | 3-Cl | i-Bu | 3-Br | i-Bu |
| 3-Cl | s-Bu | 3-Br | s-Bu | 3-Cl | s-Bu | 3-Br | s-Bu | 3-Cl | s-Bu | 3-Br | s-Bu | 3-Cl | s-Bu | 3-Br | s-Bu |
| 3-Cl | t-Bu | 3-Br | t-Bu | 3-Cl | t-Bu | 3-Br | t-Bu | 3-Cl | t-Bu | 3-Br | t-Bu | 3-Cl | t-Bu | 3-Br | t-Bu |

$X^1$ is Cl; $X^2$ is OS(O)$_2$Ph-4-Me

| Z is N | | | | Z is CH | | | | Z is CCl | | | | Z is CBr | | | |
|---|---|---|---|---|---|---|---|---|---|---|---|---|---|---|---|
| $R^3$ | $R^4$ | $R^3$ | $R^4$ | $R^3$ | $R^4$ | $R^3$ | $R^4$ | $R^3$ | $R^4$ | $R^3$ | $R^4$ | $R^3$ | $R^4$ | $R^3$ | $R^4$ |
| 3-Cl | H | 3-Br | H | 3-Cl | H | 3-Br | H | 3-Cl | H | 3-Br | H | 3-Cl | H | 3-Br | H |
| 3-Cl | Me | 3-Br | Me | 3-Cl | Me | 3-Br | Me | 3-Cl | Me | 3-Br | Me | 3-Cl | Me | 3-Br | Me |
| 3-Cl | Et | 3-Br | Et | 3-Cl | Et | 3-Br | Et | 3-Cl | Et | 3-Br | Et | 3-Cl | Et | 3-Br | Et |
| 3-Cl | n-Pr | 3-Br | n-Pr | 3-Cl | n-Pr | 3-Br | n-Pr | 3-Cl | n-Pr | 3-Br | n-Pr | 3-Cl | n-Pr | 3-Br | n-Pr |
| 3-Cl | i-Pr | 3-Br | i-Pr | 3-Cl | i-Pr | 3-Br | i-Pr | 3-Cl | i-Pr | 3-Br | i-Pr | 3-Cl | i-Pr | 3-Br | i-Pr |
| 3-Cl | n-Bu | 3-Br | n-Bu | 3-Cl | n-Bu | 3-Br | n-Bu | 3-Cl | n-Bu | 3-Br | n-Bu | 3-Cl | n-Bu | 3-Br | n-Bu |
| 3-Cl | i-Bu | 3-Br | i-Bu | 3-Cl | i-Bu | 3-Br | i-Bu | 3-Cl | i-Bu | 3-Br | i-Bu | 3-Cl | i-Bu | 3-Br | i-Bu |
| 3-Cl | s-Bu | 3-Br | s-Bu | 3-Cl | s-Bu | 3-Br | s-Bu | 3-Cl | s-Bu | 3-Br | s-Bu | 3-Cl | s-Bu | 3-Br | s-Bu |
| 3-Cl | t-Bu | 3-Br | t-Bu | 3-Cl | t-Bu | 3-Br | t-Bu | 3-Cl | t-Bu | 3-Br | t-Bu | 3-Cl | t-Bu | 3-Br | t-Bu |

$X^1$ is Br; $X^2$ is OS(O)$_2$Me

| $R^3$ | $R^4$ | Z | $R^3$ | $R^4$ | Z | $R^3$ | $R^4$ | Z | $R^3$ | $R^4$ | Z |
|---|---|---|---|---|---|---|---|---|---|---|---|
| 3-Me | H | N | 4-Me | H | CH | 3-Br | H | N | 3-CF$_3$ | H | N |
| 5-Cl | Me | CH | 3-OEt | Me | N | 4-I | Me | CH | 5-CF$_2$H | Me | CH |
| 4-n-Bu | Et | N | 2-OCF$_3$ | Et | CH | 3-CN | Et | CH | 6-CH$_3$ | Et | N |
| 5-NMe$_2$ | n-Pr | CH | 3-cyclo-Pr | n-Pr | CH | 3-NO$_2$ | n-Pr | CH | 3-CH$_2$CF$_3$ | n-Pr | CH |
| 3-OCH$_2$F | i-Pr | N | H | i-Pr | N | 3-S(O)$_2$CH$_3$ | i-Pr | CH | 6-cyclohexyl | i-Pr | CH |
| 4-OCH$_3$ | n-Bu | CH | 4-F | n-Bu | CCl | 4-SCH$_3$ | n-Bu | CH | 4-CH$_2$CH=CH$_2$ | n-Bu | CH |

$X^1$ is Br

| $R^3$ | $R^4$ | Z | $X^2$ | $R^3$ | $R^4$ | Z | $X^2$ |
|---|---|---|---|---|---|---|---|
| 3-Cl | H | N | OS(O)$_2$Et | 3-Cl | H | N | OS(O)$_2$CF$_3$ |
| 3-Br | Me | CH | OS(O)Me | 3-Br | Me | CH | OS(O)2-n-Bu |
| 3-Cl | Et | N | OP(O)(OMe)$_2$ | 3-Cl | Et | N | OP(O)(O-i-Pr)$_2$ |
| 3-Br | n-Pr | CH | OP(OMe)$_2$ | 3-Br | n-Pr | CH | OS(O)$_2$Ph-2,4,6-tri-Me |
| 3-Cl | i-Pr | N | OP(O)(OEt)$_2$ | 3-Cl | i-Pr | N | OP(O)(OPh-4-Me)$_2$ |
| 3-Br | n-Bu | CH | OP(O)(OPh)$_2$ | 3-Br | n-Bu | CH | OS(O)$_2$Ph-4-Cl |

The 3-halo-4,5-dihydro-1H-pyrazole preparation method of the present invention can be used to prepare a wide variety of compounds of Formula I that are useful as intermediates for the preparation of crop protection agents, pharmaceuticals and other fine chemicals. Exhibit 3 lists examples of 3-halo-4,5-dihydro-1H-pyrazoles which can be prepared according to the method of the present invention from corresponding 4,5-dihydro-1H-pyrazoles having OS(O)$_m$R$^1$ (e.g., OS(O)$_2$CH$_3$ or OS(O)$_2$Ph), OP(O)$_p$(OR$^2$)$_2$ (e.g., OP(O)(OMe)$_2$) or a different halogen substituent (e.g., Cl replacing Br, or Br replacing Cl), including 3-halo-4,5-dihydro-1H-pyrazoles which are useful in the preparation of products having fungicidal, herbicidal or plant growth regulant utility. These examples are to be construed as illustrative, but not limiting, of the diverse scope of applicability of the method of the present invention. Other compounds preparable according to the method of the present invention may be useful for the preparation of pharmaceutical products, such as anti-inflammatories, allergy inhibitors, anti-convulsants, sedative agents, etc.

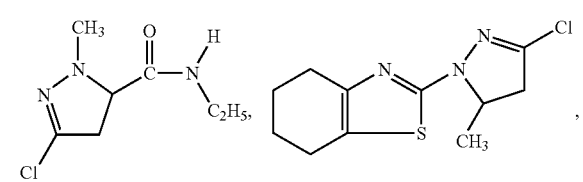

-continued
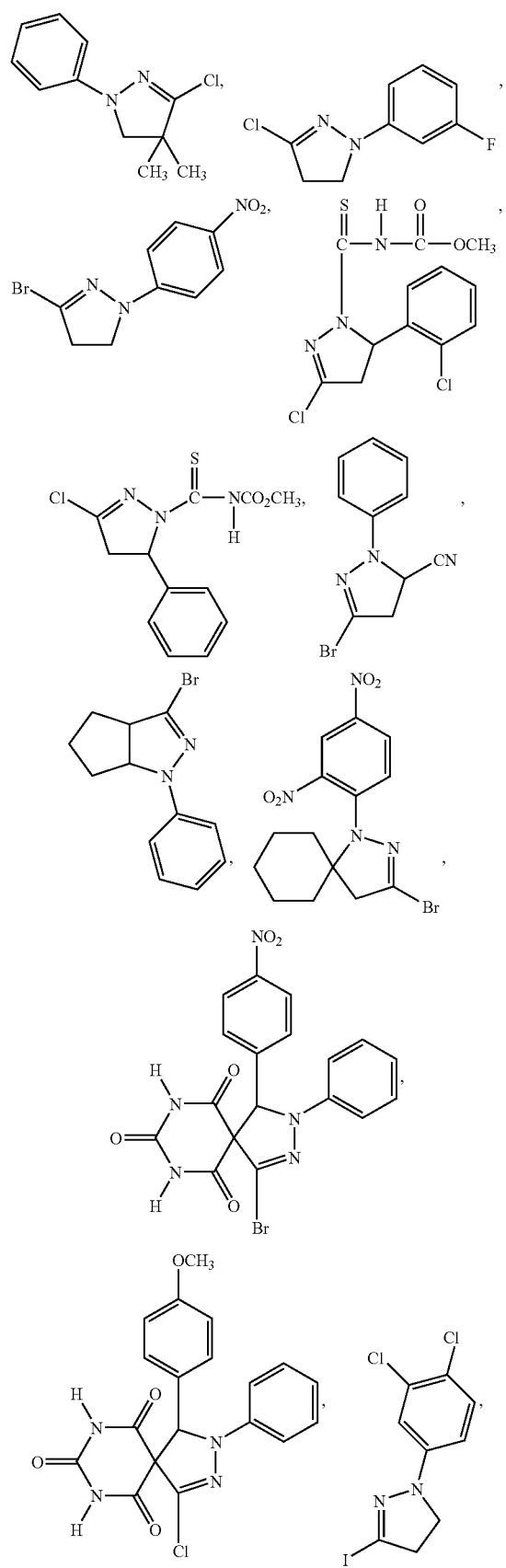
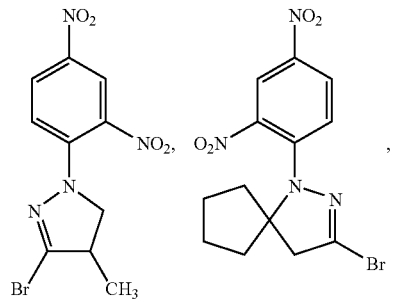
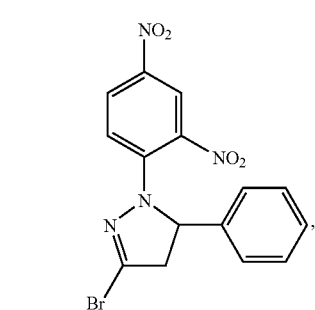
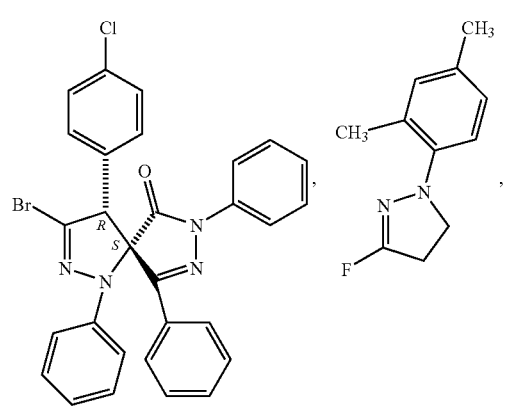
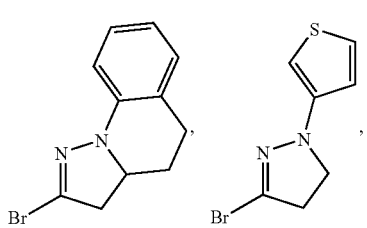
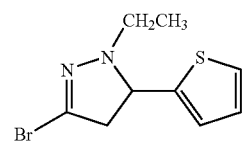
Among the compounds preparable according to the method of the present invention, compounds of Formula Ia are particularly useful for preparing compounds of Formula III

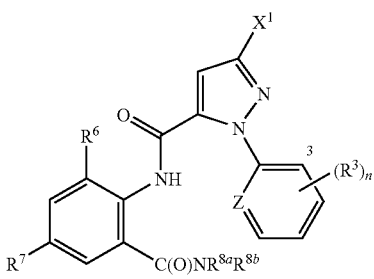

wherein Z, $X^1$, $R^3$ and n are defined as above; $R^6$ is $CH_3$, F, Cl or Br; $R^7$ is F, Cl, Br, I or $CF_3$; $R^{8a}$ is $C_1$-$C_4$ alkyl; and $R^{8b}$ is H or $CH_3$. Preferably Z is N, n is 1, and $R^3$ is Cl or Br and is at the 3-position.

Compounds of Formula III are useful as insecticides, as described, for example, in PCT Publication No. WO 01/70671, published Sep. 27, 2001, as well as in U.S. Patent Application 60/324,173, filed Sep. 21, 2001, U.S. Patent Application 60/323,941, filed Sep. 21, 2001 and U.S. Patent Application 60/369,661, filed Apr. 2, 2002. The preparation of compounds of Formula 8 and Formula III is described in U.S. Patent Application 60/400,352, filed Jul. 31, 2002 [BA9308 US PRV], and U.S. Patent Application 60/446,438, filed Feb. 11, 2003 [BA9308 US PRV1] and hereby incorporated herein in their entirety by reference; as well as in U.S. Patent Application 60/369,660, filed Apr. 2, 2002.

Compounds of Formula III can be prepared from corresponding compounds of Formula Ia by the processes outlined in Schemes 6-9.

As illustrated in Scheme 6, a compound of Formula Ia is treated with an oxidizing agent optionally in the presence of acid.

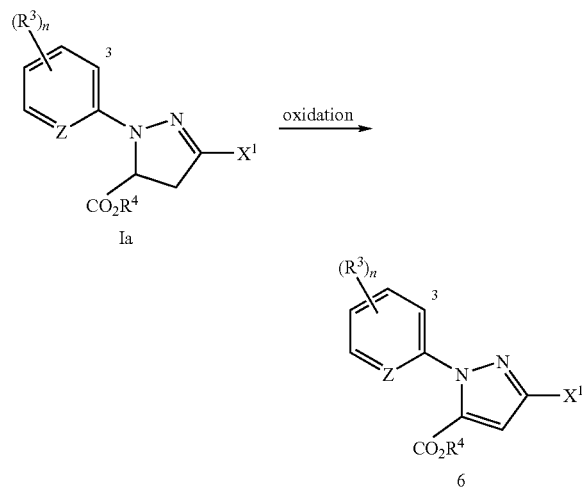

wherein $R^3$, $R^4$, Z, $X^1$ and n are as previously defined for Formula Ia.

A compound of Formula Ia wherein $R^4$ is $C_1$-$C_4$ alkyl is preferred as starting material for this step. The oxidizing agent can be hydrogen peroxide, organic peroxides, potassium persulfate, sodium persulfate, ammonium persulfate, potassium monopersulfate (e.g., Oxone®) or potassium permanganate. To obtain complete conversion, at least one equivalent of oxidizing agent versus the compound of Formula Ia should be used, preferably from about one to two equivalents. This oxidation is typically carried out in the presence of a solvent. The solvent can be an ether, such as tetrahydrofuran, p-dioxane and the like, an organic ester, such as ethyl acetate, dimethyl carbonate and the like, or a polar aprotic organic such as N,N-dimethylformamide, acetonitrile and the like. Acids suitable for use in the oxidation step include inorganic acids, such as sulfuric acid, phosphoric acid and the like, and organic acids, such as acetic acid, benzoic acid and the like. The acid, when used, should be used in greater than 0.1 equivalents versus the compound of Formula Ia. To obtain complete conversion, one to five equivalents of acid can be used. For the compounds of Formula Ia wherein Z is $CR^5$, the preferred oxidant is hydrogen peroxide and the oxidation is preferably carried out in the absence of acid. For the compounds of Formula Ia wherein Z is N, the preferred oxidant is potassium persulfate and the oxidation is preferably carried out in the presence of sulfuric acid. The reaction can be carried out by mixing the compound of Formula Ia in the desired solvent and, if used, the acid. The oxidant can then be added at a convenient rate. The reaction temperature is typically varied from as low as about 0° C. up to the boiling point of the solvent in order to obtain a reasonable reaction time to complete the reaction, preferably less than 8 hours. The desired product, a compound of Formula 6 can be isolated by methods known to those skilled in the art, including extraction, chromatography, crystallization and distillation.

Carboxylic acid compounds of Formula 6 wherein $R^4$ is H can be prepared by hydrolysis from corresponding ester compounds of Formula 6 wherein, for example, $R^4$ is $C_1$-$C_4$ alkyl. Carboxylic ester compounds can be converted to carboxylic acid compounds by numerous methods including nucleophilic cleavage under anhydrous conditions or hydrolytic methods involving the use of either acids or bases (see T. W. Greene and P. G. M. Wuts, *Protective Groups in Organic Synthesis,* 2nd ed., John Wiley & Sons, Inc., New York, 1991, pp. 224-269 for a review of methods). For compounds of Formula 6, base-catalyzed hydrolytic methods are preferred. Suitable bases include alkali metal (such as lithium, sodium or potassium) hydroxides. For example, the ester can be dissolved in a mixture of water and an alcohol such as ethanol. Upon treatment with sodium hydroxide or potassium hydroxide, the ester is saponified to provide the sodium or potassium salt of the carboxylic acid. Acidification with a strong acid, such as hydrochloric acid or sulfuric acid, yields the carboxylic acid of Formula 6 wherein $R^4$ is H. The carboxylic acid can be isolated by methods known to those skilled in the art, including extraction, distillation and crystallization.

Coupling of a pyrazolecarboxylic acid of Formula 6 wherein $R^4$ is H with an anthranilic acid of Formula 7 provides the benzoxazinone of Formula 8. In Scheme 7, a benzoxazinone of Formula 8 is prepared directly via sequential addition of methanesulfonyl chloride in the presence of a tertiary amine such as triethylamine or pyridine to a pyrazolecarboxylic acid of Formula 6 wherein $R^4$ is H, followed by the addition of an anthranilic acid of Formula 7, followed by a second addition of tertiary amine and methanesulfonyl chloride.

Scheme 7

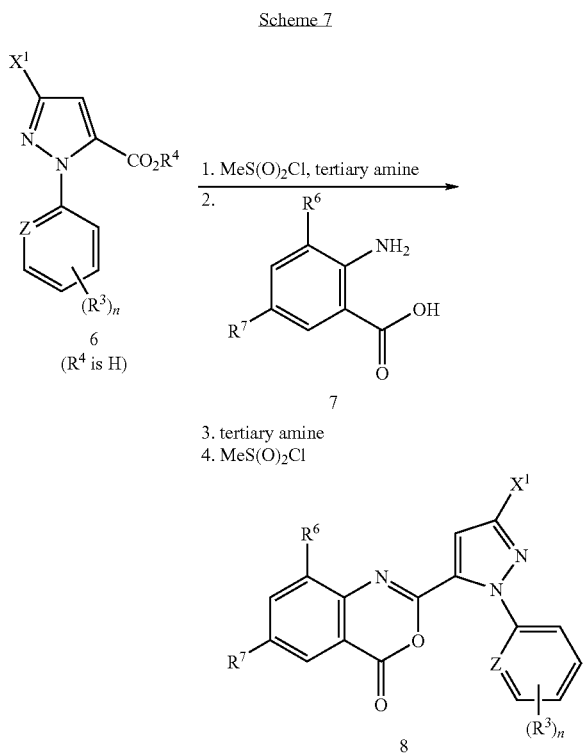

wherein $R^3$, $R^6$, $R^7$, $X^1$, Z and n are as defined for Formula III.

This procedure generally affords good yields of the benzoxazinone.

Scheme 8 depicts an alternate preparation for benzoxazinones of Formula 8 involving coupling of a pyrazole acid chloride of Formula 10 with an isatoic anhydride of Formula 9 to provide the Formula 8 benzoxazinone directly.

Scheme 8

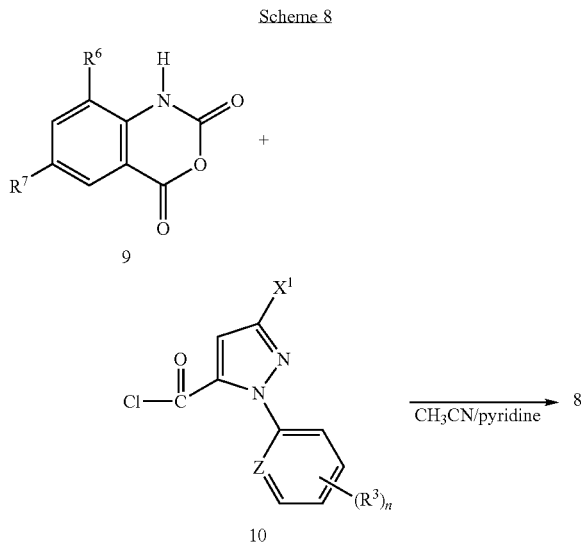

wherein $R^3$, $R^6$, $R^7$, $X^1$, Z and n are as defined for Formula III.

Solvents such as pyridine or pyridine/acetonitrile are suitable for this reaction. The acid chlorides of Formula 10 are available from the corresponding acids of Formula 6 wherein $R^4$ is H by known procedures such as chlorination with thionyl chloride or oxalyl chloride. Compounds of Formula III can be prepared by the reaction of benzoxazinones of Formula 8 with $C_1$-$C_4$ alkylamines and ($C_1$-$C_4$ alkyl)(methyl)amines of Formula 11 as outlined in Scheme 9.

Scheme 9

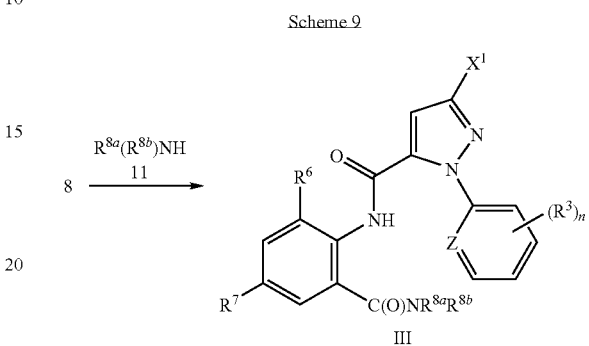

wherein $R^3$, $R^6$, $R^7$, $R^{8a}$, $R^{8b}$, $X^1$, Z and n are as previously defined.

The reaction can be run neat or in a variety of suitable solvents including acetonitrile, tetrahydrofuran, diethyl ether, dichloromethane or chloroform with optimum temperatures ranging from room temperature to the reflux temperature of the solvent. The general reaction of benzoxazinones with amines to produce anthranilamides is well documented in the chemical literature. For a review of benzoxazinone chemistry see Jakobsen et al., *Biorganic and Medicinal Chemistry* 2000, 8, 2095-2103 and references cited within. See also Coppola, *J. Heterocyclic Chemistry* 1999, 36, 563-588.

What is claimed is:
1. A compound of Formula IIa

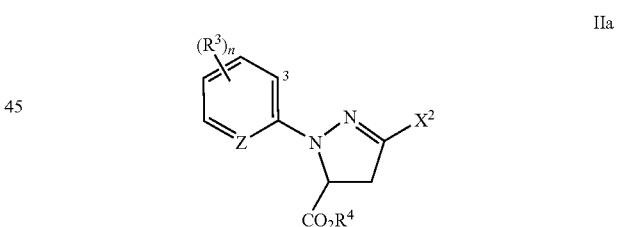

wherein
each $R^3$ is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, ($C_1$-$C_4$ alkyl)($C_3$-$C_6$ cycloalkyl)amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;
$R^4$ is H or $C_1$-$C_4$ alkyl;
$X^2$ is $OS(O)_m R^1$;
m is 1 or 2;
$R^1$ is selected from $C_1$-$C_2$ alkyl, phenyl and 4-methylphenyl;

Z is N or CR$^5$;
R$^1$ is H or R$^3$; and
n is an integer from 1 to 3.

2. A compound of claim 1 wherein R$^4$ is C$_1$-C$_4$ alkyl.

3. A compound of claim 2 wherein Z is N, n is 1, and R$^3$ is Cl or Br and is at the 3-position.

4. A compound of claim 3 wherein m is 2, and R$^1$ is phenyl or 4-methylphenyl.

5. A compound of claim 4 wherein R$^4$ is ethyl, R$^3$ is C$_1$ and R$^1$ is phenyl.

6. A compound of claim 4 wherein R$^4$ is ethyl, R$^3$ is C$_1$ and R$^1$ is 4-methylphenyl.

7. A method of preparing a compound of Formula Ia

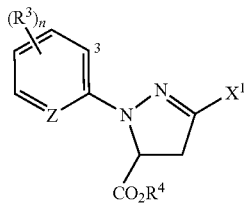

Ia wherein each R$^3$ is independently C$_1$-C$_4$ alkyl, C$_2$-C$_4$ alkenyl, C$_2$-C$_4$ alkynyl, C$_3$-C$_6$ cycloalkyl, C$_1$-C$_4$ haloalkyl, C$_2$-C$_4$ haloalkenyl, C$_2$-C$_4$ haloalkynyl, C$_3$-C$_6$ halocycloalkyl, halogen, CN, NO$_2$, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ alkylamino, C$_2$-C$_8$ dialkylamino, C$_3$-C$_6$ cycloalkylamino, (C$_1$-C$_4$ alkyl)(C$_3$-C$_6$ cycloalkyl)amino, C$_2$-C$_4$ alkylcarbonyl, C$_2$-C$_6$ alkoxycarbonyl, C$_2$-C$_6$ alkylaminocarbonyl, C$_3$-C$_8$ dialkylaminocarbonyl or C$_3$-C$_6$ trialkylsilyl;
R$^4$ is H or C$_1$-C$_4$ alkyl;
X$^1$ is halogen;
Z is N or CR$^5$;
R$^1$ is H or R$^3$; and
n is an integer from 1 to 3, comprising:
contacting a compound of Formula IIa

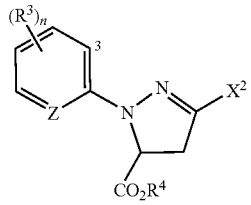

IIa wherein X$^2$ is OS(O)$_m$R$^1$;
m is 1 or 2; and
R$^1$ is selected from C$_1$-C$_2$ alkyl, phenyl and 4-methylphenyl, with a compound of formula HX$^1$ in the presence of a suitable solvent.

8. The method of claim 7 wherein R$^4$ is C$_1$-C$_4$ alkyl.

9. The method of claim 8 wherein Z is N, n is 1, and R$^3$ is Cl or Br and is at the 3-position.

10. The method of claim 8 wherein X$^1$ is Br, m is 2, and R$^1$ is phenyl or 4-methylphenyl.

* * * * *

UNITED STATES PATENT AND TRADEMARK OFFICE
CERTIFICATE OF CORRECTION

| | |
|---|---|
| PATENT NO. | : 7,705,160 B2 |
| APPLICATION NO. | : 12/004902 |
| DATED | : April 27, 2010 |
| INVENTOR(S) | : Gary David Annis |

It is certified that error appears in the above-identified patent and that said Letters Patent is hereby corrected as shown below:

Column 35, line 2, "$R^1$" should read --$R^5$--; lines 9 and 11, "$C_1$", each occurrence, should read --Cl--.

Column 36, line 7, "$R^1$" should read --$R^5$--.

Signed and Sealed this
Thirtieth Day of August, 2011

David J. Kappos
*Director of the United States Patent and Trademark Office*